United States Patent [19]
Hammond et al.

[11] Patent Number: 5,229,363
[45] Date of Patent: Jul. 20, 1993

[54] CYCLIC HEXAPEPTIDE COMPOUNDS

[75] Inventors: Milton L. Hammond, Somerville; James V. Heck, Scotch Plains; Robert A. Zambias, Springfield, all of N.J.

[73] Assignee: Merck & Co., Inc., Rahway, N.J.

[21] Appl. No.: 658,590

[22] Filed: Feb. 19, 1991

[51] Int. Cl.$^5$ .......................... A61K 37/02; C07K 7/54
[52] U.S. Cl. ........................................ 514/11; 530/317; 530/323; 530/332
[58] Field of Search ................ 530/317, 323, 332; 514/9, 11

[56] References Cited

U.S. PATENT DOCUMENTS 4,737,487  4/1988  Watts et al. ........................... 514/15
5,159,059  10/1992  Balkovec et al. ..................... 530/317

OTHER PUBLICATIONS

Ul Haque et al., Am. J. Clin. Pathol. vol. 87, No. 4, pp. 504–510 (1987).
Edman et al., Nature, vol. 334, pp. 519–522 (1988).
Robson et al., Introduction to Proteins and Protein Engineering, Elsevier, New York, pp. 323–325 (1986).
D. A. Evans et al, J. Am. Chem. Soc. 109, 7151–7157 (1987).
D. G. Melillo et al, J. Org. Chem., 52, 5143–5150 (1987).
N. Kurokawa et al, (1) J. Am. Chem. Soc. 108, 6041–6043 (1986).
N. Kurokawa et al, (2) J. Am. Chem. Soc. 108, 6043–6045 (1986).
M. Sakaitani et al, 30 2251–2254 (1989).

Primary Examiner—Y. Christina Chan
Attorney, Agent, or Firm—Alice O. Robertson; Raymond M. Speer

[57] ABSTRACT

Compounds of the formula

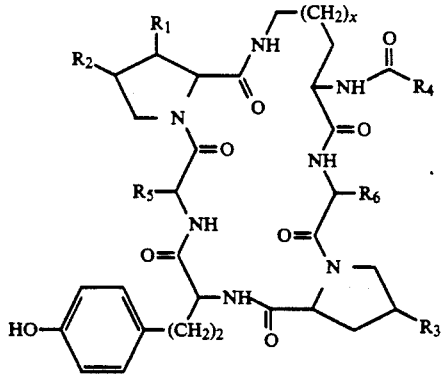

and

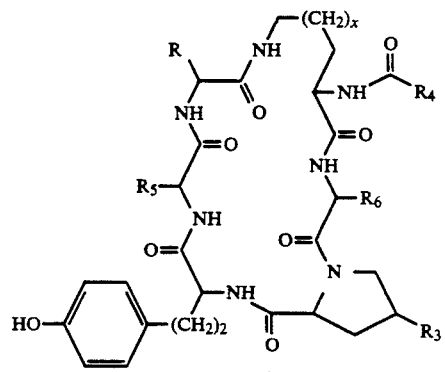

wherein $R_1$ is hydrogen or hydroxyl; $R_2$ is hydrogen; hydroxyl or methyl, $R_3$ is hydrogen or hydroxyl; $R_4$ is $C_5$–$C_{23}$ alkyl, $C_5$–$C_{23}$ alkenyl, aryl or substituted aryl; $R_5$ is —$CH_2OH$, —$CH(CH_3)OH$, —$CH(CH_2CONH_2)OH$; $R_6$ is —$CH_2OH$ or —$CH(CH_3)OH$; R is —$CH_2OH$ or —$CH(CH_3)OH$; provided that when $R_4$ is —$(CH_2)_8CH(CH_3)CH_2CH(CH_3)C_2H_5$, $R_5$ is —$CH_2OH$ or —$CH(CH_3)OH$. The compounds are useful as antimicrobial agents, especially as antifungal agents.

12 Claims, No Drawings

CYCLIC HEXAPEPTIDE COMPOUNDS

The present invention is directed to a novel cyclic hexapeptide compound represented by the structure

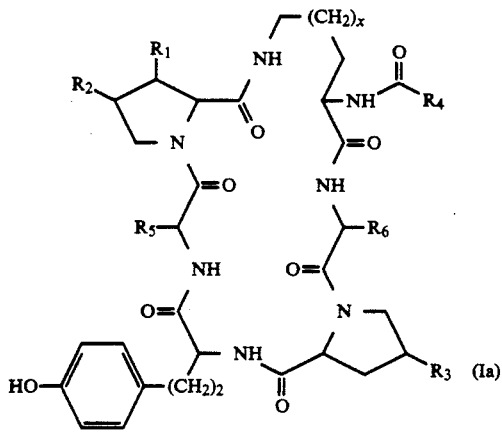

(Ia)

or

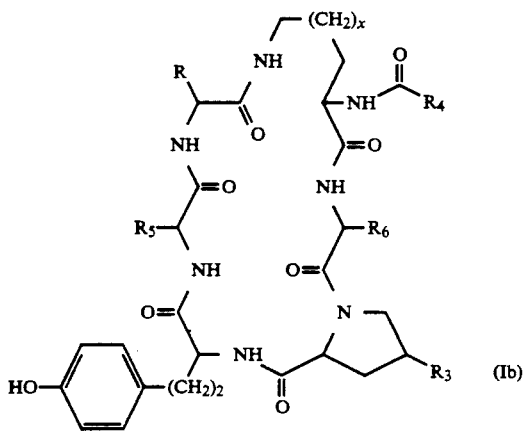

(Ib)

In this and succeeding formulas
R₁ is hydrogen or hydroxyl;
R₂ is hydrogen, hydroxyl or methyl;
R₃ is hydrogen or hydroxyl;
R₄ is $C_5$-$C_{23}$ alkyl, $C_5$-$C_{23}$ alkenyl, aryl or substituted aryl;
R₅ is —CH₂OH,

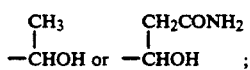

R₆ is —CH₂OH or

R is a residue of an amino acid, preferably
—CH₂OH or

and x is 1 or 2.

The foregoing structures embrace specific compounds hereinafter described in the working examples and identifiable by SEQ ID NOS: 1-15.

Representative alkyls are normal and branched octadecyl, hexadecyl, dodecyl, decyl, tetradecyl, tridecyl, pentadecyl and the like.

Representative alkenyls are 8,11-heptadecadienyl, 2-hexenyl, 4-octenyl, 7-pentadecenyl, 8-heptadecenyl, 10-heptadecenyl and the like.

Representative aryl and substituted aryl are phenyl, tolyl, xylyl, 2-ethylphenyl, 4-ethylphenyl, 4-isopropylphenyl, 4-isooctylphenyl, 4-tert-butylphenyl, 4-decylphenyl, 3-ethoxyphenyl, 4-isopropoxyphenyl, 4-(n-nonyloxy)phenyl, 4-(n-octyloxy)phenyl, 4-(n-decyloxy)phenyl, 2,4-dimethoxyphenyl, 4-(t-butoxy)phenyl, 2-methylthiophenyl, 4-(n-nonylthio)phenyl, 4-(n-octylthio)phenyl, mesityl, or other alkyl-, alkoxy- or alkylthio-substituted phenyls.

Preferred compounds are those in which R₅ and R₆ are

The expression "Compounds I" may be employed hereinafter to refer to the generic group and hence all compounds embraced by formula (I), i.e., (Ia) and (Ib).

By "residue of an amino acid" is meant a residue of any neutral amino acid. Preferred acids are serine and threonine.

In defining or discussing the peptide chain, shorthand notations conventionally employed for amino acids may be employed. Representative of but not inclusive are the following abbreviations which may be used in the present application: Orn=ornithine, Ser=serine, Glu=-glutamic acid; Pro=proline; Thr=threonine. Since the peptide chain is a synthetic one, both natural and unnatural amino acids are contemplated and not limited to the foregoing.

The products generally may be obtained in a specific stereochemical configuration since peptide synthesis can ordinarily be carried out without racemization. Both natural and unnatural amino acids are contemplated. Generally, L-amino acids have been employed to illustrate the invention in the working examples but the invention is not limited thereto.

The compounds of the present invention are generally white amorphous solids, soluble in many organic solvents such as methanol, dimethylformamide pyridine and the like.

The compounds of the present invention have antifungal and antiprotozoal activity. As antifungal agents, they are useful for the control of both filamentous fungi and yeasts. Among the filamentous fungi which may be controlled are Aspergillus species such as *Aspergillus flavus, Aspergillus fumigatus*, Neurospora species, Fusarium species, Alternaria species, and *Cochliobolus miyabeanus* and the like. They are also useful for the treatment of mycotic infections, especially those caused by *C. albicans*, and *C. tropicalis*. As antiprotozoal agents they may be useful for the control of organisms causing amebiasis such as *Entamoeba histolytica*, or malaria such as Plasmodium species, or other organisms such as Trypanosoma species, Toxaplasma species, Cryptosporidia and the like. They also may be useful for the prevention and/or treatment of *Pneumocystis carinii* infections to which immune compromised patients are especially susceptible.

The compounds may be prepared by the synthesis of a linear lipohexapeptide followed by cyclization.

Synthesis of the linear hexapeptide may be carried out by either a solid phase or solution phase method. The starting material for the synthesis is a substituted PAM (p-acetamidomethyl resin) or Merrified polystyrene based resin or the like. These methods are well-established and the use may be found summarized in the review article by George Barnay in Int. J. Peptide and Protein Research 30, 705–739 (1987) or in a chapter by G. Barnay and R. B. Merrifield in the "The Peptides" Vol. 2, p. 14–254, Academic Press, Inc., Orlando. Fla., 1979.

In the synthesis of compounds in which $R_1$ is OH and $R_2$ is hydrogen or methyl, either the PAM or Merrified polystyrene based resin may be employed. In the synthesis of compounds in which $R_2$ is OH, the required resin is prepared from chlormethyl Merrifield resin and the cesium salt of O-Bn-α-N-tBOC-(L)-4-hydroxyproline (where Bn is benzyl and tBOC is t-butyloxycarbonyl).

The synthesis of compounds (SEQ ID NOS: 1, 2, 6 and 7) in which $R_1$ is H may be carried out employing a sequence of reactions which can be seen by the following equation (illustrated with x=1):

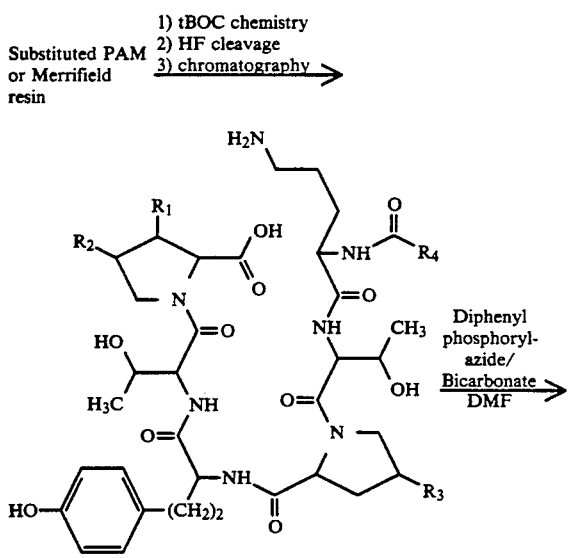

According to the above equation, the desired peptide chain may be prepared by solid phase synthesis employing tBOC chemistry comprising coupling in a stepwise fashion, a suitably protected α-N-tBOC amino acid with diisopropylcarbodiimide using hydroxybenzotriazole (HOBt) activation in N-methylpyrrolidinone. In this step, a four-fold excess of each suitably protected α-N-tBOC amino acid, diisopropyl carbodiimide, hydroxybenztriazole is employed. The calculated amount is based on the stated substitution of amino acid on the resin and on the weight of the resin used.

The intermediate tBOC protected peptide chain may be deprotected in 50 percent trifluoroacetic acid (TFA) in methylene chloride containing 2 percent anisole as scavenger. The resulting peptide chain is base washed with 20 percent diisopropylethylamine in methylene chloride. The last amino acid placed on the peptide chain is α-N-t-butyloxycarbonyl(chlorobenzyloxycarbonyl)ornithine (α-N-tBOC(Cl-Z)Orn). During the deprotection step with TFA, the Cl-Z group, i.e., the chlorobenzyloxycarbonyl group, remains on the δ-amino group while the α-amino is freed for acylation by the p-octyloxybenzoic acid side chain. The completed linear lipohexapeptide SEQ ID NOS: 16, 17, 22 and 23 is then cleaved from the resin by treatment with anhydrous HF at 0° C. This process removes all other protecting groups not removed by TFA during the regular deprotection steps and the peptide product is obtained as a hydrofluoride salt. The salt product is purified by reverse phase chromatography using acetonitrile/water mixtures buffered with 0.1% TFA.

The lipopeptide is then cyclized using diphenylphosphorylazide (DDPA) and sodium bicarbonate in DMF at low temperatures and high dilution. Purification of the cyclized compound may be carried out using reverse phase chromatography.

When $R_1$ is OH, such as in peptides (SEQ ID NOS: 3,4 and 8) containing the 3-hydroxy-4-methylproline residue, the synthesis procedure is slightly modified and may be represented by the following flow diagram:

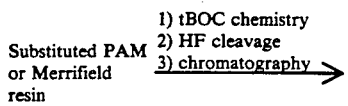

-continued

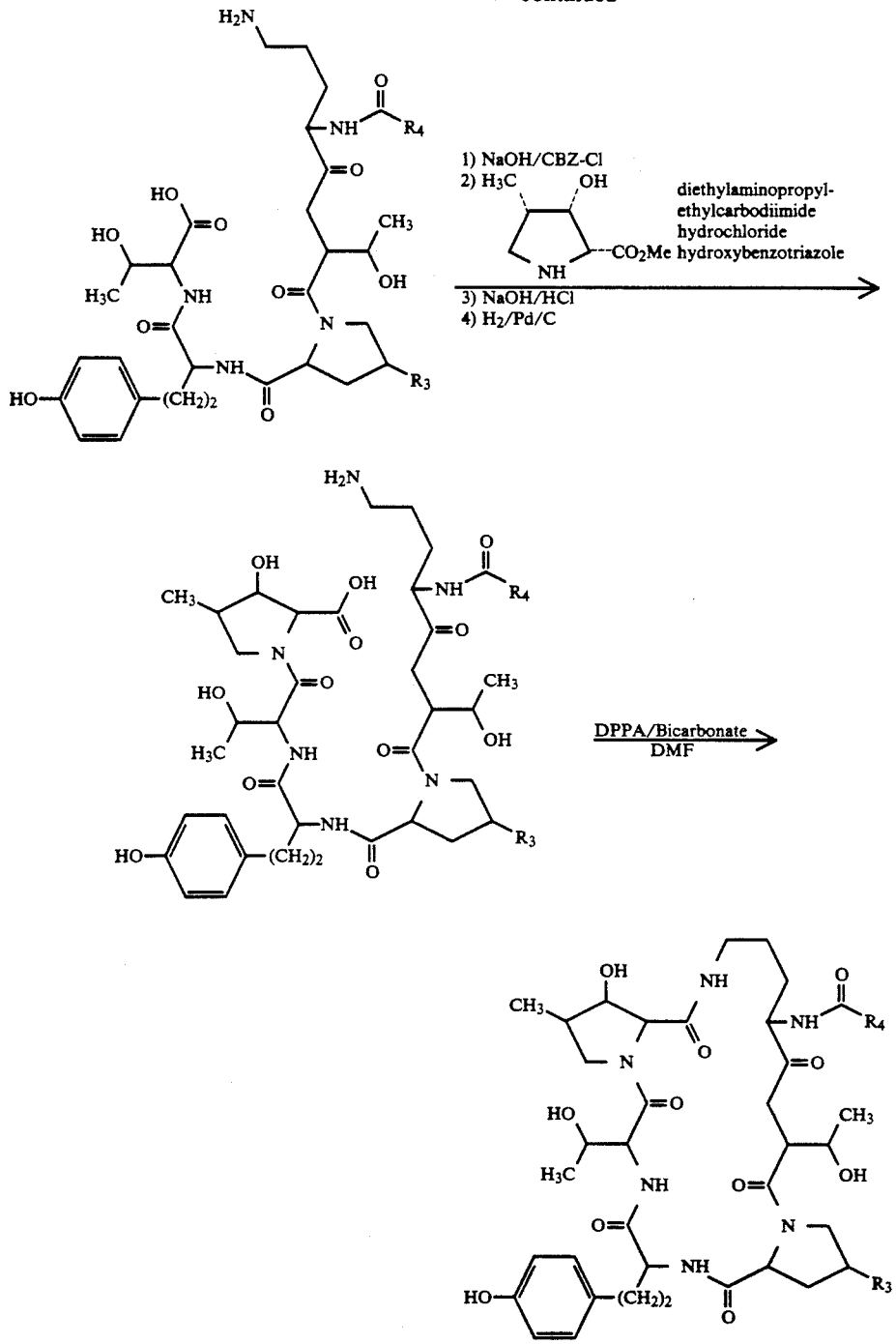

A linear pentapeptide with a C-terminal threonine residue (SEQ ID NO: 19), is prepared by a similar solid phase method as previously described. The primary amino and phenolic hydroxyl groups are protected as their benzyloxycarbonyl derivative and the protected pentapeptide coupled to the methyl ester of 3-hydroxy-4-methylproline. After coupling, the peptide is subjected to saponification conditions to remove the ester and then treated with hydrogen on Pd/C for hydrogenolysis of the CBZ group to obtain the desired linear lipohexapeptide (SEQ ID NO: 20).

The lipopeptide may then be cyclized in the manner previously described using diphenyl phosphoryl azide and sodium bicarbonate in dimethylformamide and thereafter purifying in a similar manner.

The compounds of the present invention are useful as antimicrobial agents especially as antiparasitic agents and as antifungal agents. They are most especially effective against certain fungi which are the causative agent of mycotic infections such as *Candida albicans* and *Candida tropicalis*.

The activity may be seen in an agar dilution assay employing a yeast nitrogen base dextrose agar medium. In carrying out the assay, Compounds I was solubilized in 10 percent dimethyl sulfoxide (DMSO) supplemented with one drop of tween 20 (a surface active agent, product of ICI Americas, Inc.). Twofold dilutions were made with sterile distilled water/10 percent DMSO to obtain final drug concentrations in the agar dilution assay plates ranging from 128 to 0.06 μg/ml.

The yeast cultures, maintained in yeast maltose (YM) broth, were transferred to fresh YM medium and incubated overnight at 35° C., with shaking (250 rpm). After incubation, each culture was diluted in sterile saline to yield a final concentration of $3 \times 10^5$ to $3 \times 10^6$ colony forming units (CFU)/ml.

Each prepared plate was inoculated using a Denley Multipoint Inoculator (Denley, Susex, England), which delivers approximately 0.001 milliliter to the agar surface resulting in inoculation of from $3 \times 10^2$ to $3 \times 10^3$ CFUs. The plates were incubated at 28° C., for 48 hours. The minimum inhibitory concentrations (MICs) were recorded as the lowest concentrations of drug showing no growth or less than three CFU/spot.

Useful antimycotic properties may be illustrated with the results demonstrating the superior effectiveness of Compound I against various Candida species as seen in the following table:

| Compound* | $R_1$ | $R_2$ | $R_3$ | R | C. albicans MY 1055 | C. albicans MY 1208 | C. albicans MY 1028 | C. tropicalis MY 1012 |
|---|---|---|---|---|---|---|---|---|
| A | H | H | OH | — | 8 | 4 | 4 | 0.25 |
| B | H | H | H | — | 4 | 4 | NT | 4 |
| C | H | OH | OH | — | 8 | 8 | 8 | 8 |
| D | OH | CH₃ | OH | — | 1 | 2 | 2 | 1 |
| E | — | — | OH | ** | 8 | 8 | 8 | 4 |

*Compounds of Examples I-V
**Residue of threonine

The outstanding properties are most effectively utilized when the compound is formulated into novel pharmaceutical compositions with a pharmaceutically acceptable carrier according to conventional pharmaceutical compounding techniques.

The novel compositions contain at least a therapeutic amount of the active compound. Generally, the composition contains at least 1% by weight of Compound I. Concentrate compositions suitable for dilutions prior to use may contain 90% or more by weight. The compositions include compositions suitable for rectal, topical, parenteral (including subcutaneous, intramuscular, and intravenous), pulmonary (nasal or buccal inhalation), other nasal administration, or insufflation. The compositions may be prepacked by intimately mixing Compound I with the components suitable for the medium desired.

When oral administration is to be employed, it may be with a liquid composition or a solid composition. For liquid preparations, the therapeutic agent is formulated with liquid carriers such as water, glycols, oils, alcohols, and the like, and for solid preparations such as capsules and tablets, solid carriers such as starches, sugars, kaolin, ethyl cellulose, calcium and sodium carbonate, calcium phosphate, kaolin, talc, lactose, generally with lubricant such as calcium stearate, together with binders, disintegrating agents and the like. Because of their ease in administration, tablets and capsules represent the most advantageous oral dosage form. It is especially advantageous to formulate the compositions in unit dosage form (as hereinafter defined) for ease of administration and uniformity of dosage.

When administration is to be by injection, it may be presented in unit dosage form in ampoules or in multidose containers, if necessary with an added preservative. The compositions may also take such forms as suspensions, solutions or emulsions in oily or aqueous vehicles such as 0.85 percent sodium chloride or 5 percent dextrose in water, and may contain formulating agents such as suspending, stabilizing and/or dispersing agents. Buffering agents as well as additives such as saline or glucose may be added to make the solutions isotonic. The drug also may be solubilized in alcohol/propylene glycol or polyethylene glycol for drip intravenous administration. Alternatively, the active ingredients may be in powder form for reconstituting with a suitable vehicle prior to administration.

When administration is to be by inhalation, the compound is conveniently delivered in the form of as aerosol spray presentation from pressurized packs of nebulizers. The preferred delivery system for inhalation is a metered dose inhalation (MDI) aerosol, which may be formulated as a suspension or solution of Compound A in suitable propellants, such as fluorocarbons or hydrocarbons.

The term "unit dosage form" refers to physically discrete units, each unit containing a predetermined quantity of active ingredient which singly or in multiples would produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention will generally contain from 100 to 200 milligrams of Compound I.

The following examples illustrate the invention but are not to be construed as limiting.

EXAMPLE I

Compound of SEQ ID NO: 1

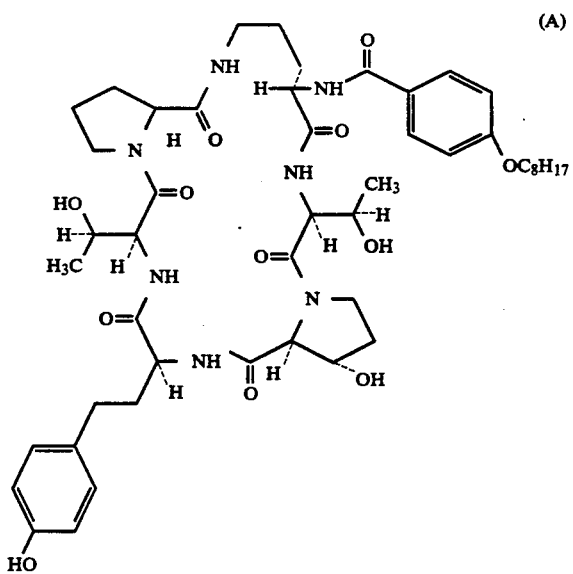

(A)

Part A. Synthesis of Linear Hexapeptide (Ai) (SEQ ID NO: 16)

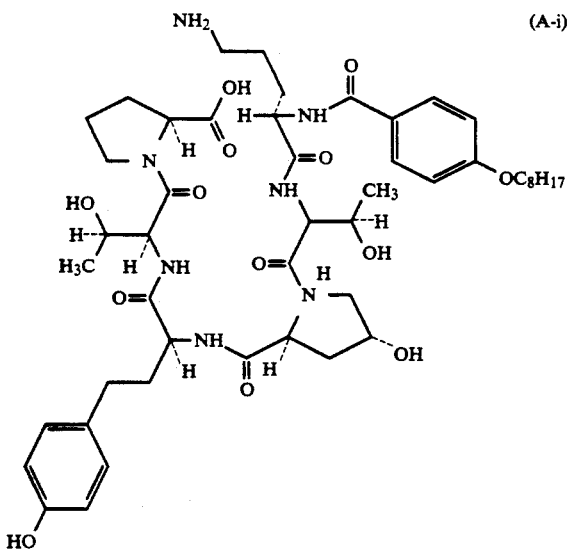

(A-i)

The synthesis of the linear peptide was carried out on a commercial (Biosearch SAM 9500) peptide synthesizer by loading in the reactor module an amino acid bearing resin and thereafter coupling the appropriate amino acid. The amino acids in the order coupled were N-BOC-O-benzyl-L-Thr (Bachem), N-BOC-O-2,6-dichloro-benzyl-L-homotyrosine (prepared as hereinafter described), N-BOC-O-benzyl-4-hydroxy-L-Pro (Bachem), N-BOC-O-benzyl-L-Thr, N-BOC-α-2-chlorobenzyloxycarbonyl-L-Orn (Bachem), and 4-octyloxybenzoic acid (prepared as hereinafter described).

625 mg of N-BOC-L-Pro-PAM resin with a nominal loading of 0.72 meq/gm (0.45 meq proline) was loaded into the reactor module of a peptide synthesizer. A four-fold excess of each amino acid component was weighed out into a reservoir and dissolved in N-methylpyrrolidinone (NMP) to a concentration of 0.6 M. One equivalent of hydroxybenzotriazole hydrate (HOBT) then was added to each of the reservoirs and dissolved by sonication. Then, each of the amino acids and octyloxybenzoic acid was charged to the reagent module which was programmed to perform the coupling in the indicated sequence.

In this procedure, the protected amino acid is coupled through the carboxyl group to the amino group on the resin with 0.4M diisopropyl carbodiimide as the coupling agent; then the protecting group is removed by washing the coupled resin with 100 milliliters of a deblocking agent consisting of 45 percent trifluoroacetic acid (TFA), 2.5 percent anisole and 52.5 percent methylene chloride by percolating nitrogen therethrough for five minutes, then recharging with fresh 100 milliliters of deblocking agent and percolating for one hour. At the end of this time, the agent is drained and the resin washed with 100 milliliters of methylene chloride, then with 100 milliliters of a base wash solution of 20 percent diisopropylethylamine in methylene chloride, followed by 100 milliliters of methylene chloride.

The reaction was carried out using the one hour single couple cycle of the Biosearch tBOC program. When the synthesis was complete, the wash solution was drained from the resin and the peptide bearing resin was dried in vacuo overnight to obtain 1.0 gram of substituted resin (95 percent of theory).

The peptide was then cleaved from the resin with anhydrous HF by transferring the peptide bearing resin to a KEL-F (DuPont) reactor and and adding 3.0 milliliters of anisole and the resin allowed to swell. Additional 0.5 millilter aliquots of anisole were added until the resin became of a consistency to be stirrable with a magnetic stir bar. The reactor was secured on an HF line, cooled with liquid nitrogen and evacuated. Then, 10.0 milliliters of anhydrous HF was distilled from cobalt (III) fluoride into the reactor. The resulting mixture was warmed to 0° C. and stirred for 30 minutes whereupon the peptide cleaved from the resin. The HF was then removed by distillation at 0° C. into a liquid nitrogen cold trap. The final traces of HF were removed with a high vacuum line. The resin was washed with diethyl ether to remove the anisole and the crude product was extracted from the resin with three 20 milliliter aliquots of 50 percent aqueous acetic acid. An HPLC analysis showed the presence of a linear lipohexapeptide of sufficient purity to be employed directly for cyclization. The retention time, $R_T$ was 7.7 minutes. The yield of the product after purification by HPLC was 258 milligrams (58%). FAB mass spectrum showed M+1 to be 954 and a 300 MHz $^1$H NMR was consistent with the desired structure.

Part B. Synthesis of the Cyclic Hexapeptide (A)

To a solution of 234 milligrams (0.246 mmol) of the linear hexapeptide (Ai), above prepared, in 25 milliliters of sieve dried (3A, 13X), degassed, dimethylformamide at −20° C. and under nitrogen atmosphere, was added by syringe, 58 μl (0.27 mmole, 1.1 eq) of diphenylphosphorylazide (DPPA) over a course of 2 minutes followed immediately by the addition in one portion of 103 milligrams (1.23 mmol, 5.0 eq) of solid sodium bicarbonate. The resulting mixture was stirred first at −20° C. for six hours, then warmed to −5° C. and stirred for 24 hours at which time HPLC analysis ("ZORBAX" siliceous microparticulate particle porous HPLC column from DuPont, 4.9 mm×25 cm C8; 40/60 H$_2$O/(9/1 CH$_3$CN/H$_2$O)) indicated completion of the reaction. The DMF solvent was removed in vacuo and the residue taken up in 10 milliliters of mobile phase solution (40/60 H$_2$O/(90/10 CH$_3$CN/H$_2$O) both containing 0.1% TFA) and injected in two portions onto a 25 mm×25 cm "ZORBAX" C8 column and eluted isocratically at 10 ml/min. The pure fractions as determined by HPLC were pooled and lyophilized to obtain 90 milligrams (40 percent yield) of pure product.

Empirical formula calcd: C$_{48}$H$_{67}$N$_7$O$_{12}$ (m.w. 935). FAB MS found: 936 (M+1).

$^1$H NMR in CD$_3$OD at 300 MHz gave the following significant signals: δ7.84 (d) (2H); 7.03 (d) (2H); 6.97 (d) (2H); 6.71 (d) (2H); 4.23 (d) (1H); 4.04 (t) (2H); 1.21 (d) (3H); 0.92 (t) (3H).

EXAMPLE II

Compound of SEQ ID NO: 2

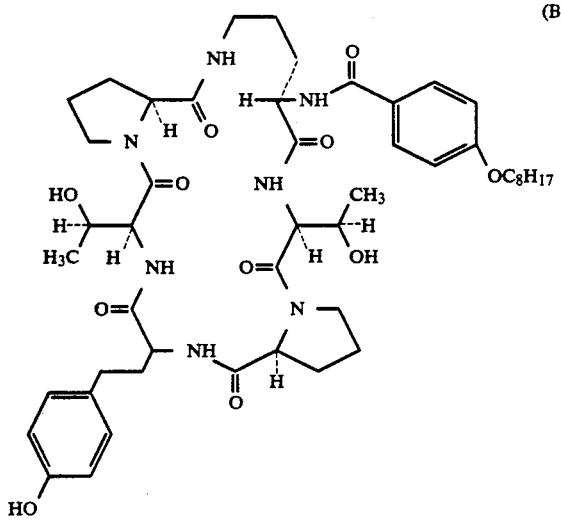

Part A. Synthesis of Linear Hexapeptide (SEQ ID NO: 17)

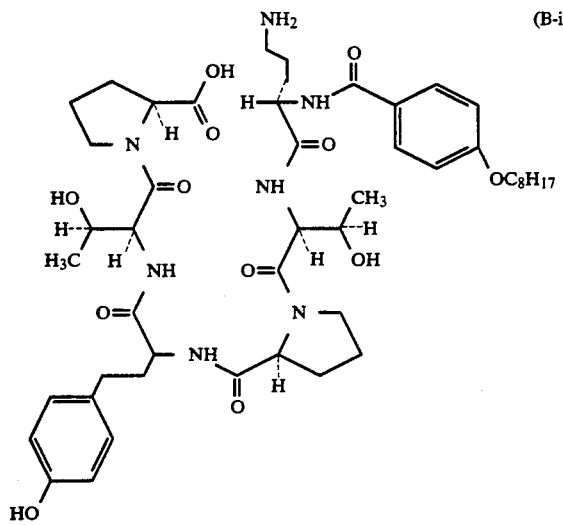

In an operation similar to that described in Example I, 712 milligrams of N-BOC-L-Pro-PAM resin, a resin with a nominal loading of 0.72 meq/gm (0.47 meq proline) was loaded into the reactor module of the peptide synthesizer.

A four-fold excess of each amino acid component to be employed in the peptide synthesis was prepared as in Example I. The amino acids in the order coupled: N-BOC-O-benzyl-L-Thr, N-BOC-O-2,6-dichlorobenzyl-L-homotyrosine, N-BOC-L-Pro (Bachem), N-BOC-O-benzyl-L-Thr, N-BOC-δ-2-chlorobenzyloxy-carbonyl-Orn, and 4-octyloxybenzoic acid. The solid phase synthesis was then performed as in Example I to obtain 1.12 grams of hexapeptide substituted resin (95% of theory).

The peptide was then cleaved from the resin with anhydrous HF in a KEL-F reactor in the manner described in Example I. After cleavage of the peptide, HF was removed in the manner described in Example I and the crude product extracted from the resin with three 20 milliliter aliquots of 50 percent aqueous acetic acid. The product was lyophilized to obtain 290 milligrams of a white amorphous solid HPLC analysis of the crude products on a ZORBAX 4.9 mm×25 cm C8 column with 45/55 H2O/(90/10 CH3CN/H2O) both containing 0.1 percent TFA mobile phase at 1.0 ml/min flow rate at ambient temperature and λ=210 showed the crude linear lipohexapeptide to contain some front and rear running impurities. The products were purified by HPLC on 25 mm×25 cm ZORBAX C8 column and eluted with 50/50 water/acetonitrile containing 0.1% TFA. The pure fractions as determined by HPLC were pooled, and the pooled fraction was lyophilized to produce a solid which amounted to 160 milligrams (36% yield).

Part B. Synthesis of the Cyclic Peptide (B)

To a solution of 143 milligrams (0.153 mmol) of the crude linear hexapeptide above prepared in 35 milliliters of dry dimethylformamide was added, under nitrogen at −20° C., 36 μl (0.168 mmol 1.1 eq) of diphenylphosphorylazide over 2 minutes, followed immediately by the addition in one portion of 65 milligrams (0.765 mmol) of solid sodium bicarbonate. The resulting mixture was stirred at −20° C. for 6 hours, then warmed to 0° C. and allowed to proceed until judged complete by HPLC analyses (56 hours) carried out on ZORBAX 4.9 mm×25 cm C8 column, eluting with 35/65 H2O/(90/10 CH3CN/H2O) both containing 0.1% TFA at a flow rate of 1.0 ml/min at ambient temperature and λ=210 nm. The DMF solution was concentrated in vacuo and the residue chromatographed on a 25 mm×25 cm ZORBAX C8 column and eluted with 46% H2O/54% CH3CN at 7.0 ml/min. The pure fractions were determined by HPLC, pooled and lyophilized to obtain 75 milligrams (54% yield) of pure product.

Empirical formula calcd: $C_{48}H_{69}N_7O_{11}$ (m.w. 919). FAB MS found: 920 (M+1).

$^1$H NMR in $CD_3OD$ at 300 MHz: δ7.81 (d) 2H; 7.01 (d) 2H; 6.98 (d) 2H; 6.70 (d) 2H; 4.76 (d) 1H; 4.02 (t) (2H); 1.19 (d) (3H); 0.90 (t) 3H.

EXAMPLE III

Compound of SEQ ID No: 3

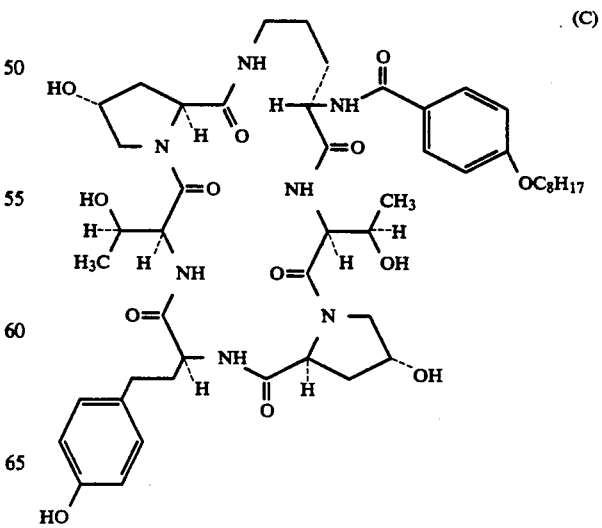

Part A. Linear Hexapeptide (C-i) (SEQ ID NO: 18)

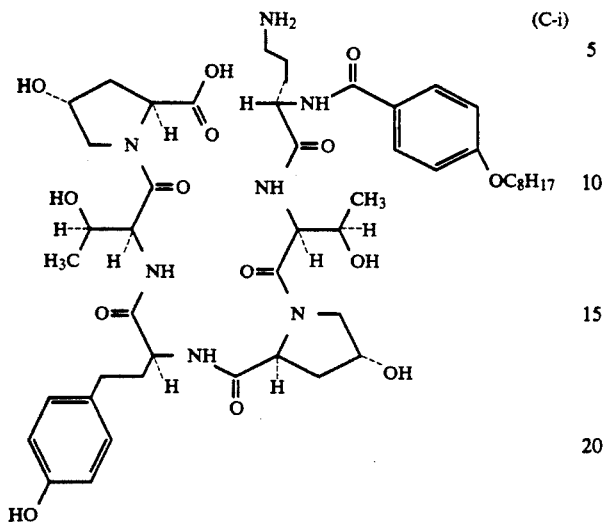
(C-i)

In an operation similar to that described in Example I, 250 mg of N-BOC-4-benzyloxy-L-Pro-Merrifield resin, prepared as described in the "Preparation of Starting Materials", was loaded into the reactor module of the peptide synthesizer. A fourfold excess of each amino acid component to be employed in the peptide synthesis was readied as in Example I and coupled in the following order: N-BOC-O-benzyl-L-Thr, N-BOC-O-2,6-dichlorobenzyl-L-homotyrosine, N-BOC-4-benzyloxy-L-Pro, N-BOC-O-benzyl-L-Thr, N-BOC-δ-2-chlorobenzyloxycarbonyl-Orn, and 4-octyloxybenzoic acid (preparation described below). The protecting groups were then removed, the resin washed and dried in vacuo to obtain 440 milligrams of substituted resin.

The peptide was then cleaved from the resin with anhydrous HF as described in Example I. After cleavage of the peptide, the crude product was extracted from the resin and the product lyophilized to obtain 150 milligrams of a white, amorphorus solid. The crude product was purified by chromatography on a 25 mm ×25 cm "ZORBAX" C8 column, eluting with 50/50 H$_2$O/CH$_3$CN containing 0.1% TFA at 10.0 ml/min. The fractions containing the desired product were pooled and lyophilized to obtain 85 milligrams (29 percent) of linear product (C-i).

Part B. Cyclic Peptide (C)

To a solution of 126 milligrams (0.130 mmol) of the crude linear hexapeptide above prepared in 35 milliliters of dry dimethylformamide was added under nitrogen at −20° C., 31 μL (0.143 mmol, 1.1 eq) of diphenylphosphorylazide over a 2 minute period, followed immediately by 55 milligrams (5.0 eq) of solid sodium bicarbonate in one addition. The resulting mixture was stirred at −20° C. for 6 hours then warmed to 0° C. and allowed to proceed for an additional 40 hours.

The DMF solution was then concentrated in vacuo. The residue was purified by flash chromatography on silica gel using 13 percent methanol in chloroform as eluant to obtain 94 milligrams of still impure material. The latter was dissolved in 5.0 milliliters of 45/55 H$_2$O/(90/10 CH$_3$CNH$_2$O) both containing 0.1 percent TFA and injected onto a 25 mm×250 mm "ZORBAX" C8 column and eluted isocratically at 7.0 ml/min. The process was repeated to obtain 28 milligrams (22 percent yield) of pure product.

Empirical formula calcd: C$_{48}$H$_{67}$N$_7$O$_{13}$ (m.w. 951). FAB MS found: 958 (M+Li).

$^1$H NMR in CD$_3$OD at 300 MHz: δ7.82 (d) 2H; 7.01 (d) 2H; 6.96 (d) 2H; 6.70 (d) 2H; 4.82 (d) 1H; 4.03 (t) (2H); 1.20 (d) (3H); 0.91 (t) 3H.

EXAMPLE IV

Compound of Sequence ID No. 4

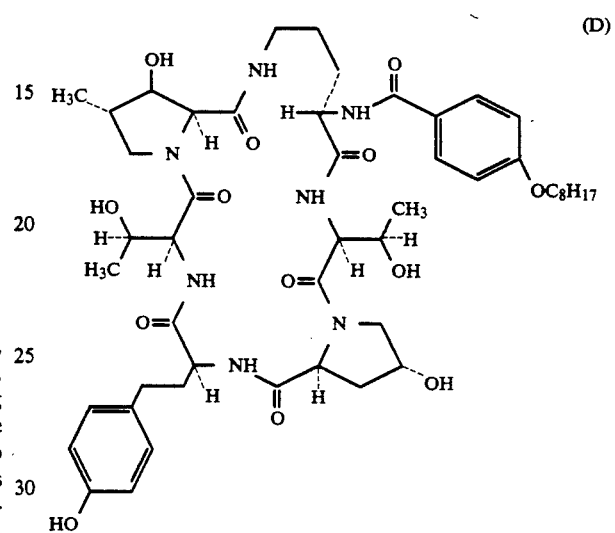
(D)

Part A. Synthesis of Linear Pentapeptide (SEQ ID No. 19)

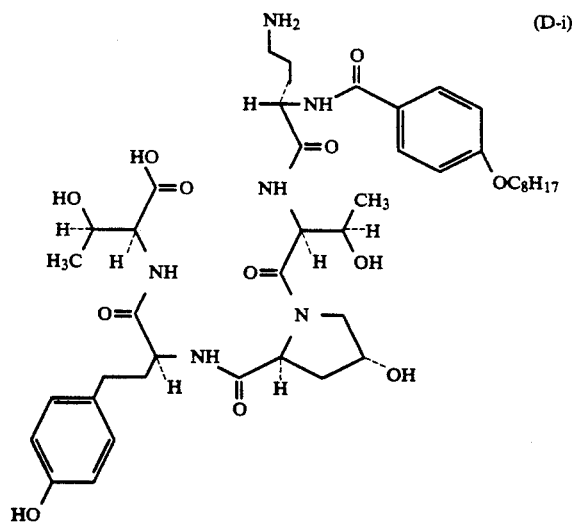
(D-i)

In an operation similar to that described in Example III, 1.0 grams of N-BOC-O-benzyl-L-Thr Merrifield resin (0.57 mmol/gm from Biosearch) was loaded into the reactor module of the synthesizer.

A fourfold molar excess of each amino acid component was prepared and coupled in the following order: N-BOC-O-2,6-dichlorobenzyl-L-homotyrosine, N-BOC-4-benzyloxy-L-Pro, N-BOC-O-benzyl-L-Thr, N-BOC-δ-2-chlorobenzyloxycarbonyl-L-Orn, and 4-octyloxybenzoic acid. Then, as described in Example I, the protected amino acid, each in turn, was coupled on the resin with 0.4M diisopropylcarbodiimide, the protecting group removed with a TFA deblocking agent solution, the resin washed with 20 percent diisopropylethylamine in methylene chloride and the washed resin collected and dried in vacuo overnight to obtain 1.55 grams of substituted resin.

The peptide was then cleaved with anhydrous HF and recovered in the manner previously described to obtain 355 milligrams (72 percent) of a white amorphous solid. The crude product was purified by subjecting to reverse phase chromatography over two 25 mm×25 cm "ZORBAX" C8 column in series and eluted with 50/50 $H_2O/CH_3CN$.

The fractions containing the purified product were pooled and lyophylized to obtain 148 milligrams (30 percent) of product.

Part B. CBZ Protection of Linear Pentapeptide (Mono and Bis) (SEQ ID No. 19)

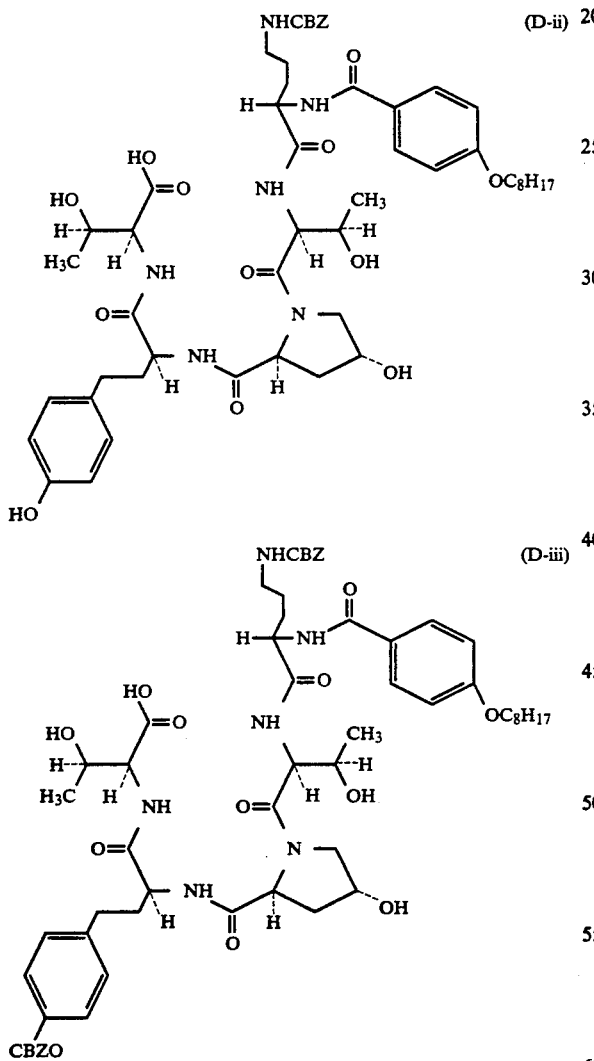

the pH between 7 and 8. This process was then repeated with identical amounts of NaOH and CBZ chloride and the pH was adjusted with 8 μl NaOH at the end. The mixture then was stirred for 10 minutes at 0° C. Thereafter, an aliquot was taken for HPLC analysis ("ZORBAX" 4.5 mm×25 cm C8 column, mobile phase: isocratic 70/30 $H_2O$/9:1 $CH_3CN:H_2O$ both containing 0.1 percent TFA, flow rate=1.0 ml/min, λ=210 nm, temperature=ambient). Analysis showed a significant amount of starting material so an additional 16 μL of 2N NaOH and 3.5 μL of CBZ chloride were added and the mixture stirred at 0° C. to obtain substantially complete reaction with the formation of mono- and bis-CBZ protected peptide in a ratio of approximately 3:1. The reaction mixture was lyophilized to obtained 183 milligrams of a crude mixture of products (D-ii and D-iii).

Part C. Coupling to obtain a Hexapeptide (SEQ ID NO: 20)

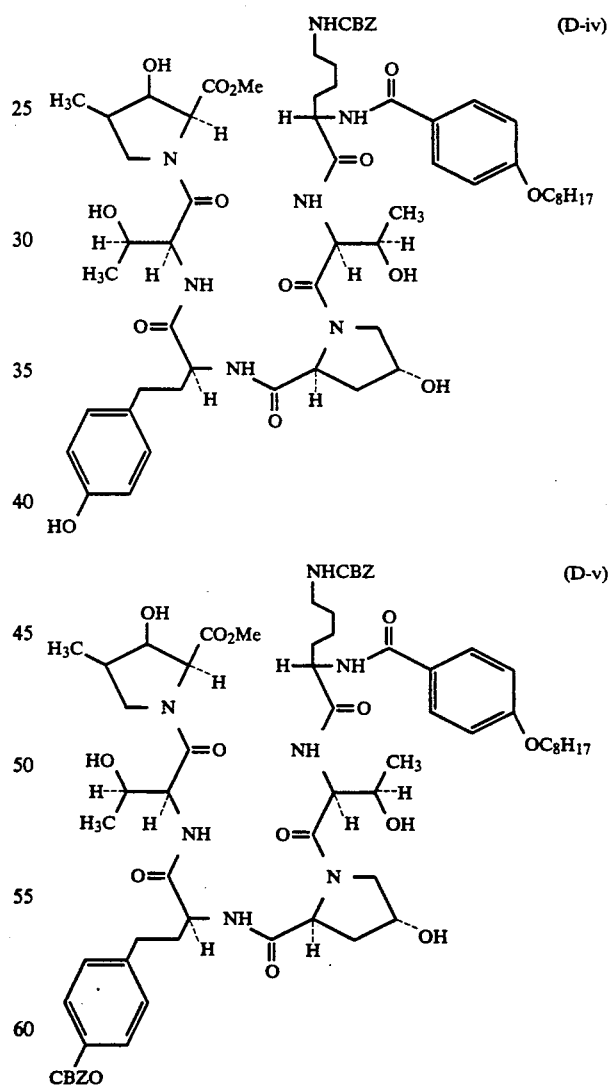

80.5 μL of 2N NaOH (0.161 mmol, 1.0 eq) was added to a 0° C. solution of 138 mg (0.161 mmol) of Compound (Di) in 10 milliliters of 20 percent aqueous t-butanol whereupon the solution became cloudy. The pH was at 7.0. Another 46.3 μL of 2N NaOH (0.0925 mmol, 0.57 eq) was added followed by 12.6 μl (0.055 eq.) CBZ-chloride. Then, 3.0 μL of 2N NaOH was added to keep To a 0° solution of 124 milligrams (0.125 mmol based on mono CBZ) of CBZ peptides and 27 milligrams (0.138 mmol 1.1 eq.) of (2S, 3S, 4S)-3-hydroxy-4-methylproline methyl ester hydrochloride in 3.0 milliliters of dry DMF under an atmosphere of nitrogen was added 19.3 μL (14 mg, 0.138 mmol) of triethylamine followed by 18 milligrams (0.131 mmol, 1.05 eq.) of hydroxybenzotriazole and 25 milligrams (0.131 mmol, 1.05 eq.) of 1-(3-dimethylaminopropyl)-2-ethylcarbodiimide hydrochloride. The reaction mixture was stirred for 2 hours at 0° C. and then overnight at room temperature. The mixture was filtered and concentrated and the residue partitioned between 3.0 milliliters of water and 14.0 milliliters of ethyl acetate. The aqueous layer was back-extracted with 1.0 milliliter of ethyl acetate and the combined organic extracts washed sequentially with 3 milliliters of 1N sodium hydrogen sulfate, 3.0 milliliters of saturated sodium bicarbonate, and 3.0 milliliters of saturated sodium chloride. The organic solution was dried over sodium sulfate, filtered and concentrated to obtain 113 milligrams (80 percent) of amorphous solids.

Part D. Mono CBZ Acid Product (D-vi) (SEQ ID NO: 20)

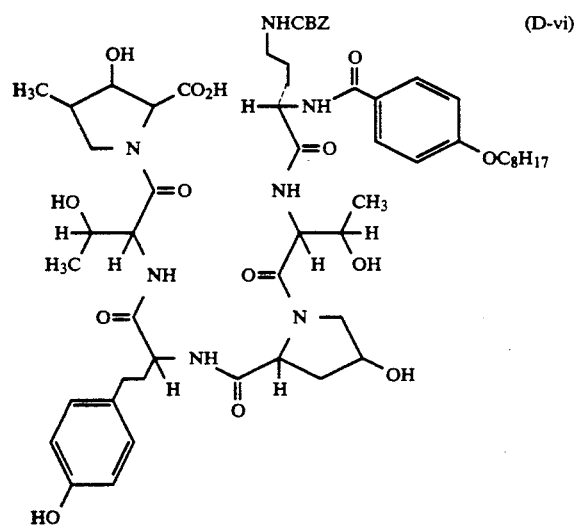

To a solution of 79 milligrams (70.7 μmols) of mono CBZ and 34 milligrams (27.2 μmols) of bis CBZ (based on HPLC ratios) in 1.6 mL of methyl alcohol was added under an atmosphere of nitrogen, 215.4 μL of 1N NaOH (2.2 eq.) and the mixture stirred for four hours. An additional aliquot of 1N NaOH then was added and the reaction allowed to proceed for another 8 hours. Then, the reaction mixture was partitioned between 25 milliliters of 1N sodium hydrogen sulfate and 75 mL ethyl acetate. The organic layer was washed, dried and concentrated to obtain 78 milligrams (70%) of the mono CBZ acid product (D-vi).

Part E. Deprotected Linear Hexapeptide (D-vii) (SEQ ID NO: 20)

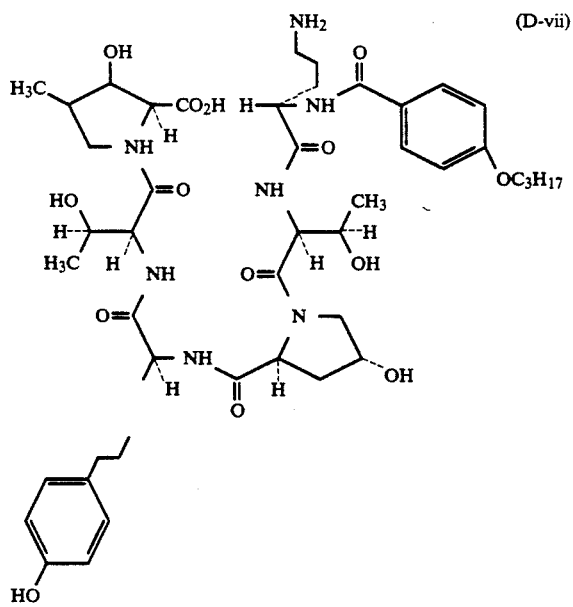

30 milligrams of 10% Pd on carbon was added, under an atmosphere of nitrogen, to a degassed solution of the crude mono CBZ (75 milligrams) in methyl alcohol. The flask was then flushed with hydrogen and allowed to stir under an atmosphere of hydrogen at room temperature overnight. Thereafter, the catalyst was filtered off and the filtrate concentrated in vacuo to obtain a residue which was dissolved in 50 mL H$_2$O/CH$_3$CN and lyophilized to produce 63 milligrams (98 percent) of amorphous white solids FAB MS found 984 (M+1) (MW=983).

Part F. Cyclic Hexapeptide (D)

To a solution of 60 milligrams (0.061 mmol) of crude linear hexapeptide in 35 milliliters of dry DMF at −20° C. under an atmosphere of nitrogen was added 31 μL (0.143 mmol, 1.1 eq) of diphenylphosphorylazide over 2 minutes followed immediately by the addition in one portion of 55 milligrams (5.0 eq) of solid sodium bicarbonate. The reaction was then warmed to 0° C. and allowed to proceed until judged complete by HPLC ("ZORBAX" 4.9 mm×25 cm C8 column, 40/60 H$_2$O/(90/10 CH$_3$CN/H$_2$O)) both containing 0.1 percent TFA. The flow rate was 0.1 ml/min at ambient temperature and detection was at a wave length of 210 nm. The DMF solution was concentrated in vacuo, subjected to flash chromatography with 13 percent methanol in chloroform to obtain 94 milligrams of still impure material and the latter subjected to reverse phase chromatography. The material was dissolved in 5.0 milliliters 40/60 H$_2$O/(90/10 CH$_3$CN/H$_2$O) both containing 0.1% TFA and injected onto a 25 mm×25 cm "ZORBAX" C8 column and eluted isocratically at 7.0 ml/min to produce 9.5 milligrams (16 percent yield) of pure product (D).

Empirical formula calcd: C$_{49}$H$_{71}$N$_7$O$_{13}$ (m.w. 965). FAB MS found: 966 (M+1).

$^1$H NMR in CD$_3$OD at 300 MHz: δ7.82 (d) (2H); 7.01 (d) (2H); 6.98 (d) (2H); 7.69 (d) (2H); 4.82 (d) (1H); 4.02 (t) (2H); 1.19 (d) (3H); 0.90 (t) (3H).

EXAMPLE V

Compound of Sequence ID NO: 5

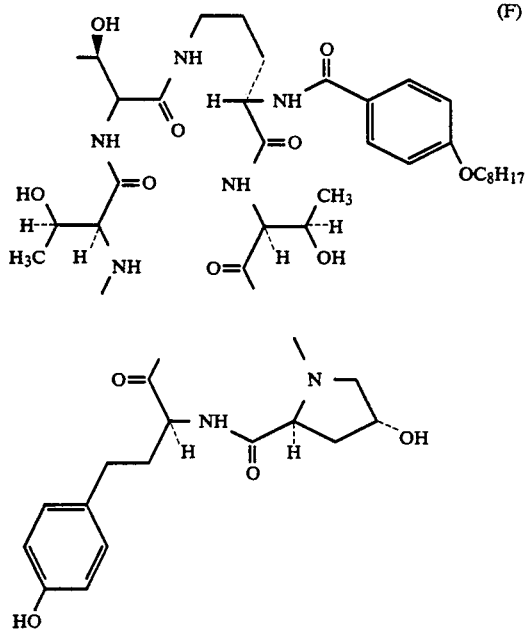

In operations carried out in a manner similar to that described in Examples I–III, the linear hexapeptide was first prepared starting with a PAM-Thr resin with a stated loading value of 0.72 meq per gram resin. In carrying out the reaction, 620 milligrams of PAM-Thr resin was loaded in the reactor module and four-fold excess of amino acids loaded in the reagent module and programmed to couple in the following order: tBOC-O-benzyl-Thr, N-tBOC-O-2,6-dichlorobenzylhomotyrosine, tBOC-O-benzyl-4-hydroxyproline; tBOC-O-benzyl-Thr, O-diClZ-t-BOC-Orn, and 4-octyloxybenzoic acid. The protecting groups were then removed with TFA solution, the resin washed with diisopropylethylamine, and the washed resin dried in vacuo to obtain 1.1 gram of resin. The peptide was then cleaved from the resin to obtain 327 milligrams (76% yield) of crude linear peptide (SEQ ID NO: 21) product.

To a solution of 305 milligrams (0.321 mole) of crude linear hexapeptide above prepared in 45 milliliters of DMF was added at −20° C., 76 microliters (0.353 mmole) of diphenyl phosphorylazide and the reaction mixture stirred for 6 hours, then the temperature increased to 0° C. and stirring continued for 6 days. The reaction mixture was filtered and the filtrate concentrated in vacuo and the residue chromatographed with 47/52 H$_2$O/(90/10 CH$_3$CN/H$_2$O) both containing 0.1 percent TFA and injected on a "ZORBAX" C8 25 mm×25 cm column at a flow rate of 10 ml/min to obtain 50 milligrams (20 percent yield) of a purified product Compound E. Empirical formula calcd: C$_{47}$H$_{69}$H$_7$O$_{13}$ (m.w. 939). FAB MS found: (940 (M+1).

$^1$H NMR in CD$_3$OD at 300 MHz: δ7.85 (d) (2H); 7.04 (d) (2H); 6.98 (d) (2H); 6.72 (d) (2H); 4.05 (t) (2H); 1.21 (d) (3H); 0.93 (t) (3H).

EXAMPLE VI

Compound of Sequence ID NO: 6

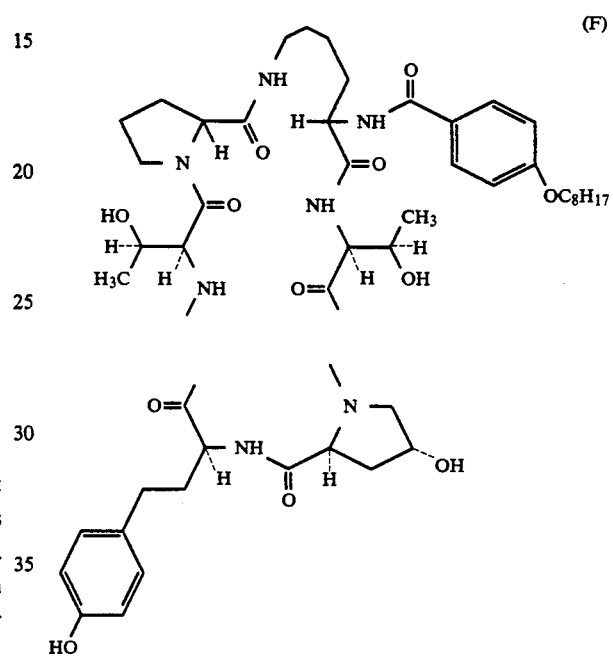

In reactions carried out in a manner described in Example I–III, a linear peptide (SEQ ID NO: 22) is first prepared by coupling the amino acids to N-BOC-L-Pro-PAM resin in the following order: N-BOC-O-benzyl-L-Thr, N-BOC-O-2,6-dichlorobenzyl-L-homotyrosine, N-BOC-O-benzyl-4-hydroxy-L-Pro, N-BOC-O-benzyl-L-Thr, N-BOC-δ-2-chloro-benzyloxycarbonyl-Lys, and 4-octyloxybenzoic acid, followed by deprotection, washing, and cleaving from the resin with HF.

To a solution of 140 milligrams of crude linear hexapeptide above prepared in dry DMF is added under nitrogen at −20° C., 35 μL of diphenyl phosphorylazide over a 2 minute period followed by addition in one portion of sodium bicarbonate. The reaction is allowed to proceed until substantially complete and the product purified by chromatography on a "ZORBAX" C8 column eluting with 40/60 water/(90/10 CH$_3$CN/H$_2$O) both containing 0.1 percent TFA. The pure fractions are pooled and lyophilized to obtain the cyclized product of formula (F).

EXAMPLE VII

Compound of Sequence ID NO: 7

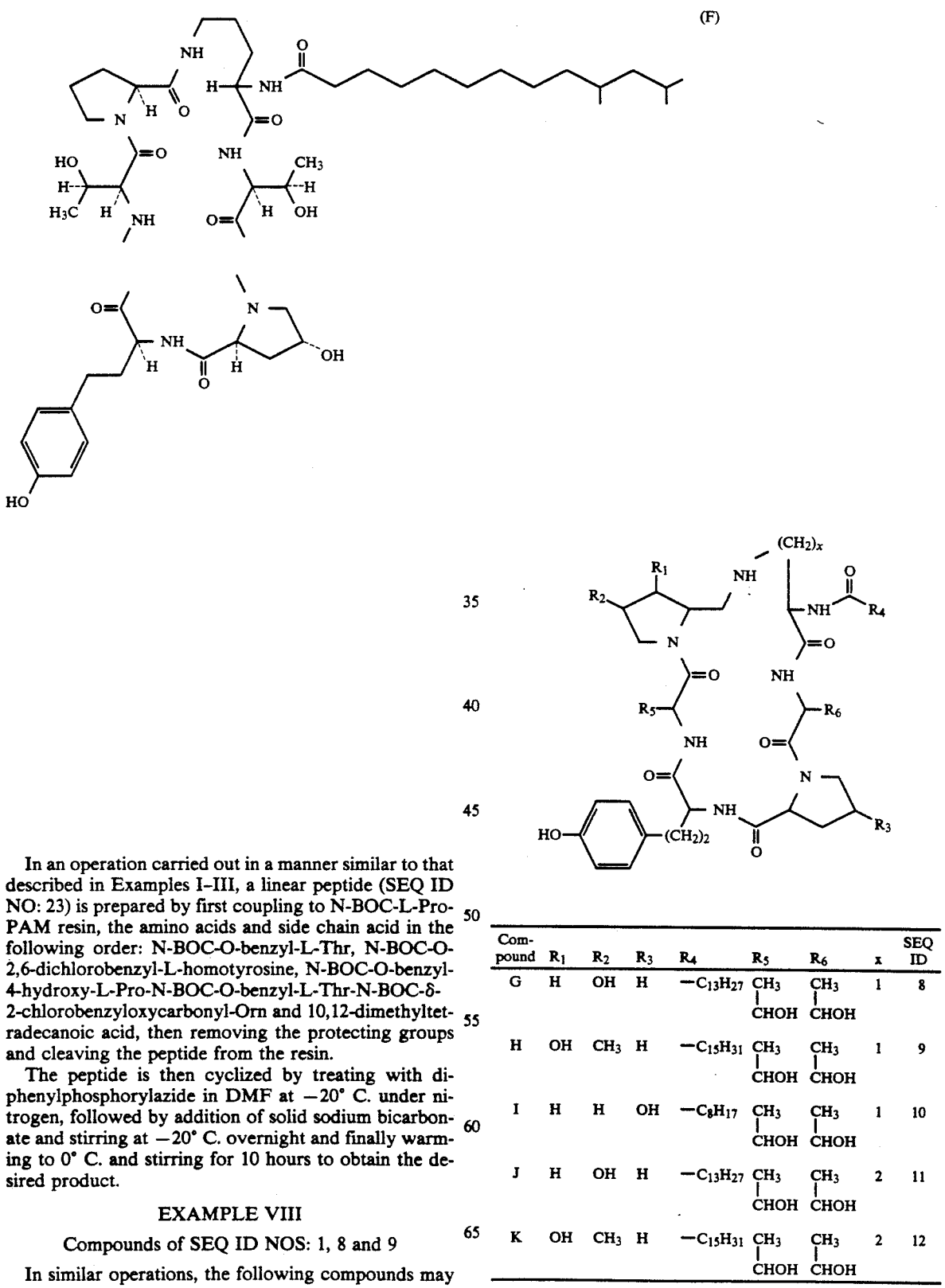

In an operation carried out in a manner similar to that described in Examples I–III, a linear peptide (SEQ ID NO: 23) is prepared by first coupling to N-BOC-L-Pro-PAM resin, the amino acids and side chain acid in the following order: N-BOC-O-benzyl-L-Thr, N-BOC-O-2,6-dichlorobenzyl-L-homotyrosine, N-BOC-O-benzyl-4-hydroxy-L-Pro-N-BOC-O-benzyl-L-Thr-N-BOC-δ-2-chlorobenzyloxycarbonyl-Orn and 10,12-dimethyltetradecanoic acid, then removing the protecting groups and cleaving the peptide from the resin.

The peptide is then cyclized by treating with diphenylphosphorylazide in DMF at −20° C. under nitrogen, followed by addition of solid sodium bicarbonate and stirring at −20° C. overnight and finally warming to 0° C. and stirring for 10 hours to obtain the desired product.

EXAMPLE VIII

Compounds of SEQ ID NOS: 1, 8 and 9

In similar operations, the following compounds may be prepared.

| Compound | $R_1$ | $R_2$ | $R_3$ | $R_4$ | $R_5$ | $R_6$ | x | SEQ ID |
|---|---|---|---|---|---|---|---|---|
| G | H | OH | H | —$C_{13}H_{27}$ | $CH_3$<br>$\|$<br>CHOH | $CH_3$<br>$\|$<br>CHOH | 1 | 8 |
| H | OH | $CH_3$ | H | —$C_{15}H_{31}$ | $CH_3$<br>$\|$<br>CHOH | $CH_3$<br>$\|$<br>CHOH | 1 | 9 |
| I | H | H | OH | —$C_8H_{17}$ | $CH_3$<br>$\|$<br>CHOH | $CH_3$<br>$\|$<br>CHOH | 1 | 10 |
| J | H | OH | H | —$C_{13}H_{27}$ | $CH_3$<br>$\|$<br>CHOH | $CH_3$<br>$\|$<br>CHOH | 2 | 11 |
| K | OH | $CH_3$ | H | —$C_{15}H_{31}$ | $CH_3$<br>$\|$<br>CHOH | $CH_3$<br>$\|$<br>CHOH | 2 | 12 |

EXAMPLE IX

Compound of Sequence ID NO: 9

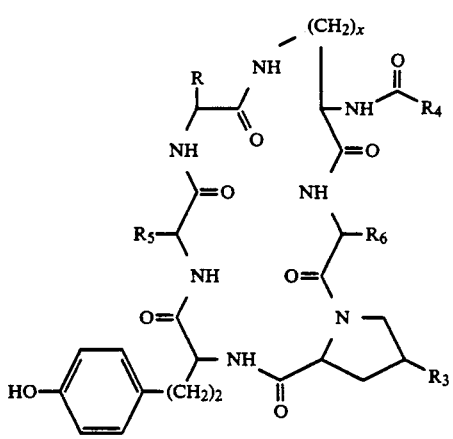

| Compound | R | R$_3$ | R$_4$ | R$_5$ | R$_6$ | x | SEQ ID NO. |
|---|---|---|---|---|---|---|---|
| L | —CH$_2$OH | OH | —C$_{16}$H$_{33}$ | CH$_3$<br>\|<br>CHOH | CH$_3$<br>\|<br>CHOH | 1 | 13 |
| M | —CH$_2$OH | OH | —C$_{14}$H$_{29}$ | CH$_2$OH | CH$_2$OH | 2 | 14 |
| N | CH$_3$<br>\|<br>—CH—OH | OH | —C$_{16}$H$_{33}$ | CH$_3$<br>\|<br>CH—OH | CH$_3$<br>\|<br>CHOH | 2 | 15 |

EXAMPLE X 1000 hard gelatin capsules, each containing 500 mg of Compound A are prepared from the following formulation:

| Compound | Grams |
|---|---|
| Compound I | 500 |
| Starch | 750 |
| Dibasic calcium phosphate hydrous | 5000 |
| Calcium stearate | 2.5 |

A uniform mixture of the ingredients is prepared by blending and used to fill two-piece hard gelatin capsules.

EXAMPLE XI 250 ml of an injectable solution are prepared by conventional procedures having the following formulation:

| Dextrose | 12.5 g |
|---|---|
| Water | 250 mL |
| Compound B | 400 mg |

The ingredients are blended and thereafter sterilized for use.

EXAMPLE XII

An aerosol composition may be prepared having the following formulation:

| | Per Canister |
|---|---|
| Compound C | 24 mg |
| Lecithin NF Liquid Concentrated | 1.2 mg |
| Trichlorofluoromethane, NF | 4.026 g |
| Dichlorodifluoromethane, NF | 12.15 g |

1000 compressed tablets each containing 500 mg of Compound D are prepared from the following formulation:

| Compound | Grams |
|---|---|
| Compound D | 500 |
| Starch | 750 |
| Dibasic calcium phosphate hydrous | 5000 |
| Calcium stearate | 2.5 |

The finely powdered ingredients are mixed well and granulated with 10% starch paste. The granulation is dried and compressed into tablets.

Preparation of Starting Materials

The protected homotyrosine and its protected counterpart have been prepared through the following sequence of reactions:

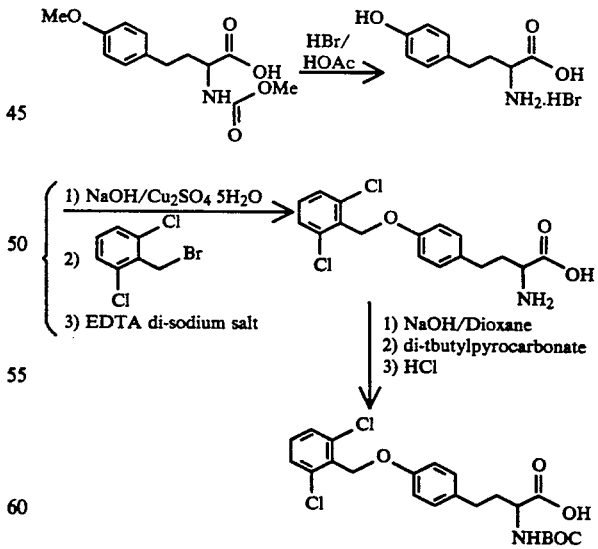

Preparation of Homotyrosine

A solution of (S)-N-methylcarbamoylhomotyrosine methyl ether (20.00 g, 74.90 mmol, prepared as described by Mellilo et al, J. Org. Chem. 52, 5143 (1987)), in 30% HBr in acetic acid (100 mL) was heated to 60°

C. for 66 hours with mechanical stirring then allowed to cool to room temperature. A solid was deposited. The reaction mixture was diluted with ether (100 mL) and the product isolated by filtration and washed with ether. The pale yellow solid was taken up in methanol with warming and diluted with ether. The solution was decanted from insoluble material, then concentrated to a yellow oil which solidified and was triturated with ether to produce the hydrobromide of homotyrosine as a white solid (18.27 g, 88%). $^1$H NMR ($\delta$): 7.06 (d, 2H, J=8.4 Hz), 6.73 (d, 2H, J=8.4 Hz), 3.96 (t, 1H, J=6.6 Hz), 2.69 (m, 2H), 2.15 (m, 2H).

Preparation of O-2,6-Dichlorobenzyl Homotyrosine

This procedure is similar to that described for tyrosine by Yamashiro and Li (JACS 95, 1310 (1973)). To a solution of NaOH (7.07 g, 176.8 mmol) in water (56 mL) was added homotyrosine hydrobromide (16.00 g, 58.0 mmol prepared as above described) and to the resulting solution was added a solution of copper (II) sulfate pentahydrate (7.236 g, 29.00 mmol) in water (28 mL). The mixture was heated to 55° C. then cooled to room temperature and diluted with methanol (240 mL). To the resulting mixture was added 2,6-dichlorobenzyl bromide (18.510 g, 77.2 mmol) and the reaction allowed to stir at room temperature for 22 hours. The green solid which had precipitated was collected by filtration, and washed sequentially with 25% water in methanol, methanol, and acetone (200 mL aliquots each). After air drying the resulting green solid (24.0 g) was added in 3 aliquots of 8 grams each to a boiling solution of 250 milliliters of water and 250 milliliters of ethanol containing EDTA (5.0 g as the disodium salt). After stirring for a few minutes at the boiling point the solution (which had a small amount of fine white solid crystallizing) was decanted from a small residual amount of heavy blue solid. The three combined solutions were combined and allowed to crystallize overnight in the refrigerator. The product was recovered by filtration and washed sequentially with water and ethanol, then dried in a dessicator under vacuum. The product is a pale yellow solid (9.38 g, 47%). $^1$H NMR ($\delta$): 7.45 (d, 2H, J=9 Hz), 7.36 (dd, 1H, J=9 Hz), 7.19 (d, 2H, J=8.4 Hz), 6.96 (d, 2H, 2.70 (m, 2H), 2.12 (m, 2H). This material was used without further purification.

Preparation of S-O-2,6-Dichlorobenzyl-N-tBOC Homotyrosine

To a mixture of aqueous sodium hydroxide (1.016 g, 25.42 mmol) in water (50 mL) dioxane (50 mL) was added O-2,6-dichlorobenzyl homotyrosine (9.00 g, 25.42 mmol) and to the resulting solution was added di-t-butylpyrocarbonate (6.10 g, 28.0 mmol). The mixture was allowed to stir at room temperature for 5 hours. At the end of this time, the mixture was concentrated to remove as much of the dioxane as possible. A precipitate formed during the concentration. To the resulting aqueous mixture was added ethyl acetate. (200 mL) and the reaction mixture acidified with 2N HCl (25 mL). The organic layer was dried (MgSO$_4$) and concentrated. This material was purified by flash chromatography using 3% methanol in methylene chloride containing 1% acetic acid as eluant to produce S-O-2,6-dichlorobenzyl-N-t-BOC homotyrosine as a pale yellow solid (8.38 g, 73%) after two concentrations from toluene to remove residual acetic acid. $^1$H NMR ($\delta$): 7.45 (d, 1H, J=8.7 Hz), 7.45 (d, 1H, J=7.2 Hz), 7.35 (dd, 1H, J=7.2, 8.7 Hz), 7.15 (d, 2H, J=8.7 Hz), 6.95 (d, 2H, J=8.7 Hz), 5.26 (s, 2H), 4.05 (m, 1H), 2.66 (m, 2H), 2.07 (m, 1H), 1.92 (m, 1H), 1.46 (s, 9H).

Preparation of N-BOC-4-benzyloxy-L-Pro Merrifield Resin

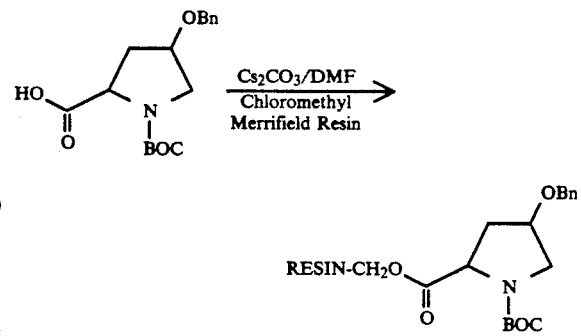

To a solution of 3.45 grams (10.72 mmol) N-BOC-4-benzyloxy-L-Pro (Bachem) in 25 milliliters of absolute ethanol was added 5.0 ml of H$_2$O. The pH was then adjusted to 7.7 with 2.0M Cs$_2$CO$_3$ (27.0 ml, 5.4 mmol). The solution was then diluted with 100 milliliters ethanol and concentrated down to dryness in vacuo. The residue was azeotroped 3 times with 50 ml toluene and dried in a vacuum dessiccator over P$_2$O$_5$. The resulting cesium salt was then placed in dry DMF (65 ml) and stirred with 8.0 grams of chloromethyl-Merrifield resin (1.34 mmol Cl/g., 10.72 mmol, 200–400 mesh from Biorad) for 4 hours. The resin was then washed with DMF, DMF: H$_2$O 1:1, DMF, and finally methyl alcohol. After drying in vacuo the final weight of the resin was 10.9 g.

Preparation of p-(n-octyloxy)benzoic acid 19.20 grams (150 mmol) of 4-hydroxybenzoic acid was added to an aqueous solution of sodium hydroxide (12.00 grams in 120 milliliters of water) and the mixture stirred until all the solid had dissolved. The solution was added in a portionwise manner over a period of about 5 minutes so that the temperature of the reaction mixture did not exceed 85° C. to 480 milliliters of dimethylsulfoxide which had previously been warmed to 80° C. To the resulting solution was added dropwise 28.95 grams (150 mmol) of n-octylbromide over about five to ten minutes. The mixture was then allowed to cool to room temperature over a period of about four hours; then it was poured into 1200 milliliters of ice water. Concentrated hydrochloric acid (30 mL) then was added to precipitate the desired octyloxybenzoic acid. The precipitate was recovered by filtration, washed with water and thereafter recrystallized from isopropanol to obtain octyloxybenzoic acid, m.p. 97°–102° C.

---

What is claimed is:

1. A compound represented by the structure

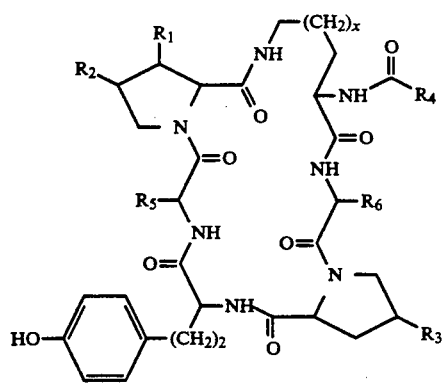
(a)

or

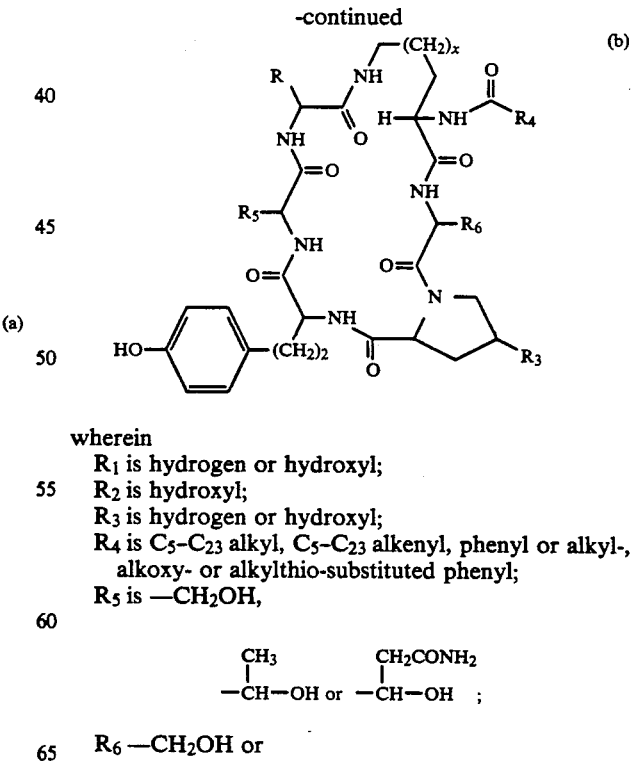
(b)

wherein
$R_1$ is hydrogen or hydroxyl;
$R_2$ is hydroxyl;
$R_3$ is hydrogen or hydroxyl;
$R_4$ is $C_5$-$C_{23}$ alkyl, $C_5$-$C_{23}$ alkenyl, phenyl or alkyl-, alkoxy- or alkylthio-substituted phenyl;
$R_5$ is —$CH_2OH$, $$\underset{-CH-OH}{\overset{CH_3}{|}} \text{ or } \underset{-CH-OH}{\overset{CH_2CONH_2}{|}} ;$$

$R_6$ —$CH_2OH$ or

R is —CH$_2$OH or $$-\overset{CH_3}{\underset{|}{CH}}OH;$$

and x is 1 or 2; and including compounds identified by SEQ ID NOS: 1-15.

2. A compound represented by the structure

[chemical structure showing cyclic peptide with R$_1$, R$_2$, R$_3$, R$_4$, R$_5$, R$_6$ substituents, (CH$_2$)$_x$, (CH$_2$)$_2$, and HO-phenyl groups]

wherein

R$_1$ is hydrogen or hydroxyl;

R$_2$ is hydroxyl;

R$_3$ is hydrogen or hydroxyl;

R$_4$ is C$_5$-C$_{23}$ alkyl, C$_5$-C$_{23}$ alkenyl, phenyl or alkyl-, alkoxy- or alkylthio-substituted phenyl;

R$_5$ is —CH$_2$OH, $$-\overset{CH_3}{\underset{|}{CH}}-OH \text{ or } -\overset{CH_2CONH_2}{\underset{|}{CH}}-OH \quad ;$$

R$_6$ —CH$_2$OH or $$-\overset{CH_3}{\underset{|}{CH}}-OH;$$

x is 1 or 2; and including compounds identified by SEQ ID NOS: 1-4 and 6-12.

3. A compound represented by the structure

[chemical structure showing cyclic peptide with R, R$_3$, R$_4$, R$_5$, R$_6$ substituents, (CH$_2$)$_x$, (CH$_2$)$_2$, and HO-phenyl groups]

wherein

R is —CH$_2$OH or $$-\overset{CH_3}{\underset{|}{CH}}OH;$$

R$_3$ is hydrogen or hydroxyl;

R$_4$ is C$_5$-C$_{23}$ alkyl, C$_5$-C$_{23}$ alkenyl, phenyl, or alkyl-, alkoxy- or alkylthio-substituted phenyl;

R$_5$ is —CH$_2$OH, $$-\overset{CH_3}{\underset{|}{CH}}-OH \text{ or } -\overset{CH_2CONH_2}{\underset{|}{CH}}-OH \quad ;$$

R$_6$ is —CH$_2$OH or $$-\overset{CH_3}{\underset{|}{CH}}-OH;$$

and x is 1 or 2; and including compounds identified by SEQ ID NOS: 5, 13, 14 and 15.

4. A compound according to claim 2 wherein R$_5$ and R$_6$ are $$-\overset{CH_3}{\underset{|}{CH}}OH;$$

and including compounds identified by SEQ ID NOS: 1-4 and 6-12.

5. A compound according to claim 3 wherein R$_5$ and R$_6$ are $$-\overset{CH_3}{\underset{|}{CH}}OH;$$

and including compounds identified by SEQ ID NOS: 5 and 12.

6. A compound according to claim 2 wherein R$_1$ is OH, R$_3$ is OH, R$_4$ is p-octyloxyphenyl, R$_5$ is $$-\overset{CH_3}{\underset{|}{CH}}-OH,$$

R$_6$ is

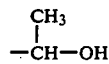

and x is 1; said compound identified by SEQ ID NO: 4.

7. A compound according to claim 2 wherein $R_1$ is H, $R_2$ is OH, $R_3$ is OH, $R_4$ is p-octyloxyphenyl, $R_5$ is

$R_6$ is

and x is 1; said compound identified by SEQ ID NO. 4.

8. A compound according to claim 2 wherein $R_1$ is H, $R_3$ is OH, $R_4$ is p-octyloxyphenyl, $R_5$ is

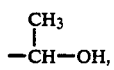

$R_6$ is

and x is 1; said compound identified by SEQ ID NOS: 1 and 7.

9. A compound according to claim 2 wherein $R_1$ is H, $R_3$ is H, $R_4$ is p-octyloxyphenyl, $R_5$ is

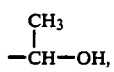

$R_6$ is

and x is 1; said compound identified by SEQ ID NO: 2.

10. A compound according to claim 3 wherein R is

$R_3$ is OH, $R_4$ is p-octyloxyphenyl, $R_5$ is

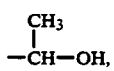

$R_6$ is

and x is 1; said compound identified by SEQ ID NO: 5.

11. An antimycotic composition comprising a therapeutically effective amount of a compound represented by the structure

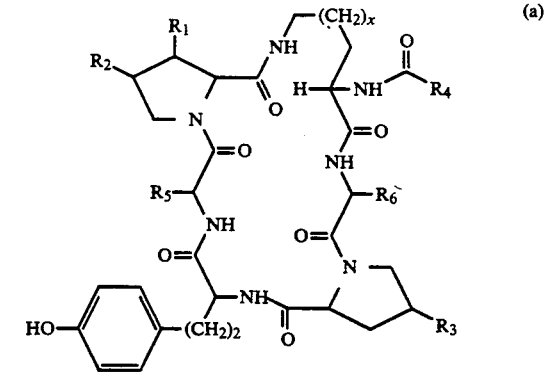

or

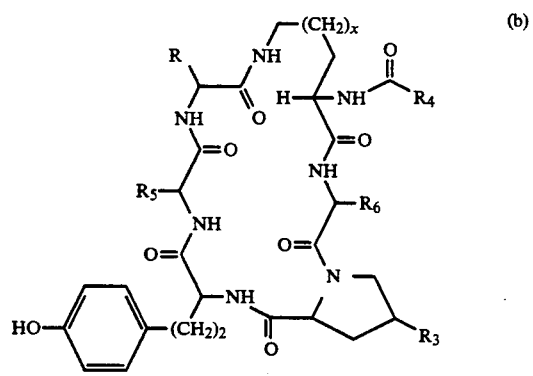

wherein
$R_1$ is hydrogen or hydroxyl;
$R_2$ is hydroxyl;
$R_3$ is hydrogen or hydroxyl;
$R_4$ is $C_5$-$C_{23}$ alkyl, $C_5$-$C_{23}$ alkenyl, phenyl or alkyl-, alkoxy- or alkylthio-substituted phenyl;
$R_5$ is —$CH_2OH$,

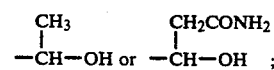

$R_6$ is —$CH_2OH$ or

R is —$CH_2OH$ or

and
x is 1 or 2; and including compounds identified by SEQ ID NOS: 1-15. said compound in admixture with a pharmaceutically acceptable carrier.

12. A method for controlling mycotic infections comprising administering an antifungal amount of the composition of claim 11.

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:1:

Xaa  Thr  Xaa  Xaa  Thr  Pro
    1                       5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:2:

Xaa  Thr  Pro  Xaa  Thr  Pro
    1                       5

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:3:

Xaa  Thr  Xaa  Xaa  Thr  Xaa
    1                       5

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:4:

Xaa  Thr  Xaa  Xaa  Thr  Xaa
    1                       5

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( x i ) SEQUENCE DESCRIPTION: SEQ ID NO:5:

Xaa  Thr  Xaa  Xaa  Thr  Thr
    1                       5

( 2 ) INFORMATION FOR SEQ ID NO:6:

( i ) SEQUENCE CHARACTERISTICS:
    ( A ) LENGTH: 6 amino acids
    ( B ) TYPE: amino acid
    ( C ) STRANDEDNESS: unknown
    ( D ) TOPOLOGY: circular ( i i ) MOLECULE TYPE: peptide ( x i ) SEQUENCE DESCRIPTION: SEQ ID NO:6:

Lys Thr Xaa Xaa Thr Pro
1          5

( 2 ) INFORMATION FOR SEQ ID NO:7:

( i ) SEQUENCE CHARACTERISTICS:
    ( A ) LENGTH: 6 amino acids
    ( B ) TYPE: amino acid
    ( C ) STRANDEDNESS: unknown
    ( D ) TOPOLOGY: circular ( i i ) MOLECULE TYPE: peptide ( x i ) SEQUENCE DESCRIPTION: SEQ ID NO:7:

Xaa Thr Xaa Xaa Thr Pro
1          5

( 2 ) INFORMATION FOR SEQ ID NO:8:

( i ) SEQUENCE CHARACTERISTICS:
    ( A ) LENGTH: 6 amino acids
    ( B ) TYPE: amino acid
    ( C ) STRANDEDNESS: unknown
    ( D ) TOPOLOGY: circular ( i i ) MOLECULE TYPE: peptide ( x i ) SEQUENCE DESCRIPTION: SEQ ID NO:8:

Xaa Thr Pro Xaa Thr Xaa
1          5

( 2 ) INFORMATION FOR SEQ ID NO:9:

( i ) SEQUENCE CHARACTERISTICS:
    ( A ) LENGTH: 6 amino acids
    ( B ) TYPE: amino acid
    ( C ) STRANDEDNESS: unknown
    ( D ) TOPOLOGY: circular ( i i ) MOLECULE TYPE: peptide ( x i ) SEQUENCE DESCRIPTION: SEQ ID NO:9:

Xaa Thr Pro Xaa Thr Xaa
1          5

( 2 ) INFORMATION FOR SEQ ID NO:10:

( i ) SEQUENCE CHARACTERISTICS:
    ( A ) LENGTH: 6 amino acids
    ( B ) TYPE: amino acid
    ( C ) STRANDEDNESS: unknown
    ( D ) TOPOLOGY: circular ( i i ) MOLECULE TYPE: peptide ( x i ) SEQUENCE DESCRIPTION: SEQ ID NO:10:

Xaa Thr Xaa Xaa Thr Pro
1         5

( 2 ) INFORMATION FOR SEQ ID NO:11:

( i ) SEQUENCE CHARACTERISTICS:
( A ) LENGTH: 6 amino acids
( B ) TYPE: amino acid
( C ) STRANDEDNESS: unknown
( D ) TOPOLOGY: circular ( i i ) MOLECULE TYPE: peptide ( x i ) SEQUENCE DESCRIPTION: SEQ ID NO:11:

Lys Thr Pro Xaa Thr Xaa
1               5

( 2 ) INFORMATION FOR SEQ ID NO:12:

( i ) SEQUENCE CHARACTERISTICS:
( A ) LENGTH: 6 amino acids
( B ) TYPE: amino acid
( C ) STRANDEDNESS: unknown
( D ) TOPOLOGY: circular ( i i ) MOLECULE TYPE: peptide ( x i ) SEQUENCE DESCRIPTION: SEQ ID NO:12:

Lys Thr Pro Xaa Thr Xaa
1               5

( 2 ) INFORMATION FOR SEQ ID NO:13:

( i ) SEQUENCE CHARACTERISTICS:
( A ) LENGTH: 6 amino acids
( B ) TYPE: amino acid
( C ) STRANDEDNESS: unknown
( D ) TOPOLOGY: circular ( i i ) MOLECULE TYPE: peptide ( x i ) SEQUENCE DESCRIPTION: SEQ ID NO:13:

Xaa Thr Xaa Xaa Thr Ser
1               5

( 2 ) INFORMATION FOR SEQ ID NO:14:

( i ) SEQUENCE CHARACTERISTICS:
( A ) LENGTH: 6 amino acids
( B ) TYPE: amino acid
( C ) STRANDEDNESS: unknown
( D ) TOPOLOGY: circular ( i i ) MOLECULE TYPE: peptide ( x i ) SEQUENCE DESCRIPTION: SEQ ID NO:14:

Lys Ser Xaa Xaa Ser Ser
1               5

( 2 ) INFORMATION FOR SEQ ID NO:15:

( i ) SEQUENCE CHARACTERISTICS:
( A ) LENGTH: 6 amino acids
( B ) TYPE: amino acid
( C ) STRANDEDNESS: unknown
( D ) TOPOLOGY: circular ( i i ) MOLECULE TYPE: peptide ( x i ) SEQUENCE DESCRIPTION: SEQ ID NO:15:

Lys Thr Xaa Xaa Thr Thr
1               5

( 2 ) INFORMATION FOR SEQ ID NO:16:

( i ) SEQUENCE CHARACTERISTICS:
( A ) LENGTH: 6 amino acids (B) TYPE: amino acid
(C) STRANDEDNESS: unknown
(D) TOPOLOGY: linear (i i) MOLECULE TYPE: peptide (x i) SEQUENCE DESCRIPTION: SEQ ID NO:16:

Xaa  Thr  Xaa  Xaa  Thr  Pro
1                    5

(2) INFORMATION FOR SEQ ID NO:17:

(i) SEQUENCE CHARACTERISTICS:
(A) LENGTH: 6 amino acids
(B) TYPE: amino acid
(C) STRANDEDNESS: unknown
(D) TOPOLOGY: linear (i i) MOLECULE TYPE: peptide (x i) SEQUENCE DESCRIPTION: SEQ ID NO:17:

Xaa  Thr  Pro  Xaa  Thr  Pro
1                    5

(2) INFORMATION FOR SEQ ID NO:18:

(i) SEQUENCE CHARACTERISTICS:
(A) LENGTH: 6 amino acids
(B) TYPE: amino acid
(C) STRANDEDNESS: unknown
(D) TOPOLOGY: linear (i i) MOLECULE TYPE: peptide (x i) SEQUENCE DESCRIPTION: SEQ ID NO:18:

Xaa  Thr  Xaa  Xaa  Thr  Xaa
1                    5

(2) INFORMATION FOR SEQ ID NO:19:

(i) SEQUENCE CHARACTERISTICS:
(A) LENGTH: 5 amino acids
(B) TYPE: amino acid
(C) STRANDEDNESS: unknown
(D) TOPOLOGY: linear (i i) MOLECULE TYPE: peptide (x i) SEQUENCE DESCRIPTION: SEQ ID NO:19:

Xaa  Thr  Xaa  Xaa  Thr
1                    5

(2) INFORMATION FOR SEQ ID NO:20:

(i) SEQUENCE CHARACTERISTICS:
(A) LENGTH: 6 amino acids
(B) TYPE: amino acid
(C) STRANDEDNESS: unknown
(D) TOPOLOGY: linear (i i) MOLECULE TYPE: peptide (x i) SEQUENCE DESCRIPTION: SEQ ID NO:20:

Xaa  Thr  Xaa  Xaa  Thr  Xaa
1                    5

(2) INFORMATION FOR SEQ ID NO:21:

(i) SEQUENCE CHARACTERISTICS:
(A) LENGTH: 6 amino acids
(B) TYPE: amino acid
(C) STRANDEDNESS: unknown ( D ) TOPOLOGY: linear ( i i ) MOLECULE TYPE: peptide ( x i ) SEQUENCE DESCRIPTION: SEQ ID NO:21:

Xaa Thr Xaa Xaa Thr Thr
1               5

( 2 ) INFORMATION FOR SEQ ID NO:22:

( i ) SEQUENCE CHARACTERISTICS:
      ( A ) LENGTH: 6 amino acids
      ( B ) TYPE: amino acid
      ( C ) STRANDEDNESS: unknown
      ( D ) TOPOLOGY: linear ( i i ) MOLECULE TYPE: peptide ( x i ) SEQUENCE DESCRIPTION: SEQ ID NO:22:

Lys Thr Xaa Xaa Thr Pro
1               5

( 2 ) INFORMATION FOR SEQ ID NO:23:

( i ) SEQUENCE CHARACTERISTICS:
      ( A ) LENGTH: 6 amino acids
      ( B ) TYPE: amino acid
      ( C ) STRANDEDNESS: unknown
      ( D ) TOPOLOGY: linear ( i i ) MOLECULE TYPE: peptide ( x i ) SEQUENCE DESCRIPTION: SEQ ID NO:23:

Xaa Thr Xaa Xaa Thr Pro
1               5